(12) United States Patent
Salama (10) Patent No.: US 7,727,530 B2
(45) Date of Patent: Jun. 1, 2010

(54) ANTI-CANCER COMPOSITION COMPRISING PROLINE OR ITS DERIVATIVES AND AN ANTI-TUMOUR ANTIBODY

(76) Inventor: Zoser B. Salama, Ansgarstr. 13, 13465 Berlin (DE)

( * ) Notice: Subject to any disclaimer, the term of this patent is extended or adjusted under 35 U.S.C. 154(b) by 0 days.

(21) Appl. No.: 11/147,648

(22) Filed: Jun. 8, 2005

(65) Prior Publication Data

US 2005/0276810 A1 Dec. 15, 2005

Related U.S. Application Data

(60) Provisional application No. 60/578,832, filed on Jun. 14, 2004.

(51) Int. Cl.
*A61K 39/395* (2006.01)
*A61K 31/40* (2006.01)
*A61K 31/401* (2006.01)

(52) U.S. Cl. .................................... 424/155.1; 514/359

(58) Field of Classification Search ........................ None
See application file for complete search history.

(56) References Cited

U.S. PATENT DOCUMENTS 5,665,371 A    9/1997  Hoerrmann
5,837,283 A *  11/1998 McDonald et al. .......... 424/450
6,153,643 A    11/2000 Hoerrmann

FOREIGN PATENT DOCUMENTS

| CA | 2548391 A1 | 6/2005 |
| CA | 2548605 A1 | 6/2005 |
| GB | 2171302 A | 8/1986 |
| WO | WO2005056005 A1 | 6/2005 |
| WO | WO2005058816 A1 | 6/2005 |

OTHER PUBLICATIONS

Fernando et al (Seminars in Oncology, Jun. 2003, 30; Suppl 6; p. 39-50).*
Stratagene catalog 1988, p. 39.*
Stedman's Online Medical Dictionary (p. 1-3).*
Zips et al. (2005, In Vivo, 19:1-7).*
Gopal et al, J Lab Clinical Medicine, 1999, 134:445-450.*

* cited by examiner

*Primary Examiner*—Laura B Goddard
(74) *Attorney, Agent, or Firm*—Joyce V. Natzmer; Pequignot + Myers (57) ABSTRACT

The present invention relates to a pharmaceutical composition comprising of proline or proline derivatives or their salts, esters, isomers, racemates, enantiomeres or prodrugs together with an anti-cancer ligand, preferably an antibody directed to a tumour antigen. The invention is also directed to the use of proline or proline derivatives or their salts, esters, isomers or prodrugs for the manufacture of a pharmaceutical composition for treating cancer and to a method of cancer treatment by administering said composition.

3 Claims, 5 Drawing Sheets

ANTI-CANCER COMPOSITION COMPRISING PROLINE OR ITS DERIVATIVES AND AN ANTI-TUMOUR ANTIBODY

CROSS REFERENCE TO RELATED APPLICATIONS

This application claims the benefit of U.S. provisional application 60/578,832, filed Jun. 14, 2004.

BACKGROUND OF THE INVENTION

The present invention relates to a pharmaceutical composition comprising of proline or proline derivatives or their salts, esters, isomers or prodrugs together with an anti-cancer ligand, preferably an antibody directed to a tumour antigen. The invention is also directed to the use of proline or proline derivatives or their salts, esters, isomers or prodrugs for the manufacture of a pharmaceutical composition for treating cancer and to a method of cancer treatment by administering said composition.

Cancer is a significant health problem in the world. Although advances have been made in cancer detection and treatment, no vaccine or other universally successful preventive or therapeutic method is currently available. Management of the disease currently relies on a combination of early diagnosis and aggressive treatment, which may include one or more of a variety of therapies such as surgery, radiotherapy, chemotherapy and hormone therapy. While such therapies provide benefit to many patients, a high mortality continues to be observed for many cancers. The development of improved anti-tumour agents would facilitate cancer prevention and treatment.

Unfortunately, cancer is the second leading cause of death, behind heart disease, in both men and women. In the fight against cancer, numerous techniques have been developed and are the subject of current research directed to understanding the nature and cause of the disease and to providing methods for the control or cure thereof.

Although thousands of potential anti-cancer agents have been evaluated, the treatment of human cancer remains fraught with complications which often present an array of suboptimal treatment choices. As such, chemotherapeutic agents which possess little or no toxicity, which are inexpensive to obtain or manufacture, which are well tolerated by the patient, and which are easily administered would be a desirable addition to the therapeutic modalities currently available to the oncologist. Agents that will selectively sensitize malignant tissue to allow lower doses of radiation or therapy to achieve the same therapeutic effect with less damage to healthy tissues are also desirable.

Similarly, agents which prevent cancer from occurring or reoccurring are also desirable. The present invention remedies these needs by providing such chemotherapeutic and sensitizing agents.

SUMMARY OF THE INVENTION

Therefore, the technical problem underlying the present invention is to provide alternative or better modified compounds which demonstrate anti-cancer activity and from these compounds generate a pharmaceutical composition which could then be used as an anti-cancer treatment. It is also an object of the present invention to provide an anti-cancer composition which can be administered following the occurrence of multidrug resistance.

The problem of the invention is solved by the provision of the embodiments as defined in the claims.

Surprisingly it has been discovered that the combination of proline or a proline derivative, e.g. cis-4-hydroxy-L-proline, and an anti-cancer ligand, preferably an antibody directed against an antigen (receptor) of a tumour cell, is useful in treatment of cancer or a cancerous condition. A synergistic effect has been found with these combinations. The combination compositions are effective in inhibiting survival and/or growth of cancer cells and/or for inhibiting undesirable cell growth in general.

This invention further provides pharmaceutical compositions, which contain a therapeutically effective amount of proline or proline derivatives or their salts, esters, isomers or prodrugs in combination with an anti-tumour antibody, and methods of treatment employing said compound combinations. In particular, this invention relates to methods of treating cancer by administration of proline or a proline derivative, preferably cis-4-hydroxy-L-proline, 4-hydroxy-1-methyl-proline, 1-methyl-4-phenylamino-carbonyloxy-proline or 1-methyl-4-phenylamino-carbonyloxy-proline, or one of the salts, isomers, esters or prodrugs thereof in combination with an anti-tumour antibody preferably a monoclonal or a bispecific antibody. Other preferred proline derivatives which may be used according to the invention are cis-4-hydroxymethyl-L-proline, trans-4-hydroxymethyl-D-proline, trans-4-hydroxymethyl-L-proline, trans-4-methyl-L-proline and cis-3-Amino-L-proline or any of their corresponding salts. Proline and its derivatives, as used according to the invention, are well known compounds which are commercially available. The preferred proline derivatives used include esters, especially methyl, ethyl, propyl, isopropyl, butyl or isobutyl esters.

The antibodies used are in a preferred embodiment of the invention monoclonal antibodies and are selected from the group comprising Trastuzumab (Herceptin), Cetuximab, Rituximab, Avastatin or an EGFR-mAb. The antibodies used are well known and commercially available antibodies directed to tumour antigens.

According to the invention it is also possible to use bispecific antibodies and/or multi-specific antibodies.

The invention is also directed to a method of treatment of cancer when multidrug resistance has occurred by administration of anti-tumour/anti-cancer drugs and/or the combination composition as described above.

Accordingly, the present invention provides a method for the combination of proline or its isoforms or derivatives thereof with antibodies which are directed against cancer-antigens and therefore have the ability to inhibit abnormal cell growth, in particular, to inhibit tumour cell growth and inhibit angiogenesis and the vascularization of endothelial cells.

Also claimed is a kit for inhibiting abnormal cell growth comprising of the two active substances of the anti-cancer composition, especially the CHP, 4-hydroxy-1-methyl-proline or 1-methyl-4-phenylamino-carbonyloxy-proline, or the salt, ester, isomer or prodrug and the anti-cancer antibody. The proline or any of its derivatives, or the salt, ester, isomer or prodrug is stored in a separate container to the anti-cancer antibody within the kit. Also included is information on how to use each part of the kit. By keeping the two active substances of the pharmaceutical composition separate, it is possible to administer the substances in different schemes (simultaneously or sequentially).

The invention further relates to a method of modification of tumour cell receptors, wherein the tumour cell is treated in vitro or in vivo with the combination composition of the invention or with proline or proline derivatives or their salts, esters, isomers or prodrugs.

Before the present compositions, formulations, and methods are described, it is to be understood that this invention is not limited to the particular methods, compositions, and cells described herein, as such methods, compositions, and cells may, of course, vary. It is also to be understood that the terminology used herein is for the purpose of describing particular embodiments only, and is not intended to limit the scope of the present invention which is only defined by the appended claims.

DETAILED DESCRIPTION OF VARIOUS AND PREFERRED EMBODIMENTS

As used herein, and including the appended claims, singular forms of words such as "a," "an," and "the" include their corresponding plural referents unless the context clearly dictates otherwise. Thus, e.g., reference to "an organism" includes one or more different organisms, reference to "a cell" includes one or more of such cells, and reference to "a method" includes reference to equivalent steps and methods known to a person of ordinary skill in the art, and so forth.

Unless otherwise defined, all technical and scientific terms used herein have the same meaning as commonly understood by a person of ordinary skill in the art to which this invention belongs. Although methods and materials similar or equivalent to those described herein can be used in the practice or testing of the present invention, suitable methods and materials are described below. All publications, patent applications, patents, and other references discussed above are provided solely for their disclosure prior to the filing date of the present application. Nothing herein is to be construed as an admission that the invention is not entitled to antedate such disclosure by virtue of its prior invention. All publications, patent applications, patents, and other references mentioned herein are incorporated by reference in their entirety including all figures and drawings.

Prior to setting forth the invention it may be helpful to an understanding thereof to set forth definitions of certain terms to be used hereinafter.

A "patient" for the purposes of the present invention includes both humans and other animals, particularly mammals, and other organisms. Thus the methods are applicable to both human therapy and veterinary applications. In the preferred embodiment the patient is a mammal, the most preferred being a human.

The term "animal" refers to an organism with a closed circulatory system of blood vessels and includes birds, mammals and crocodiles. The term "animal" used here also includes human subjects.

The term "angiogenesis" refers to the generation of new blood vessels into cells, tissue, organs or tumours.

The term "metastasis" refers to the process by which tumour cells are spread to distant parts of the body. The term is also used herein to refer to a tumour that develops through the metastatic process.

The term "contacting" is used herein interchangeably with the following: combined with, added to, mixed with, passed over, incubated with, flowed over, etc. Moreover, the compounds of present invention can be "administered" by any conventional method such as, for example, parenteral, oral, topical and inhalation routes as described herein.

As used herein, the term "safe and effective amount" refers to the quantity of a component that is sufficient to yield a desired therapeutic response without undue adverse side effects (such as toxicity, irritation, or allergic response) commensurate with a reasonable benefit/risk ratio when used in the manner of this invention. What is meant by the term "therapeutically effective amount" is the amount of a compound of the present invention which is effective in yielding the desired therapeutic response. For example, an amount which is effective in delaying the growth of a cancer, either a sarcoma or lymphoma or which causes the cancer to shrink or not metastasize. The specific amount which is safe and therapeutically effective will vary depending on such factors as the particular type of condition being treated, the physical condition of the patient, the type of mammal being treated, the duration of the treatment, the nature of concurrent therapy (if any), and the specific formulations employed and the structure of the compounds or its derivatives.

"An anti-angiogenic" amount refer to an amount of a compound or composition which is effective in depressing, suppressing or inhibiting angiogenesis or which results in the amelioration of symptoms associated with an angiogenic disease. The desired result can be either a subjective relief of a symptom(s) or an objectively identifiable improvement in the recipient of the dosage, a decrease in the vascularization of endothelial cells or a decrease in the rate of angiogenesis as noted by a clinician or other qualified observer.

The terms "treating cancer," "therapy," and the like refer generally to any improvement in the mammal having the cancer wherein the improvement can be ascribed to treatment with the compounds of the present invention. The improvement can be either subjective or objective. For example, if the mammal is human, the patient may note improved vigour or vitality or decreased pain as subjective symptoms of improvement or response to therapy. Alternatively, the clinician may notice a decrease in tumour size or tumour burden based on physical exam, laboratory parameters, tumour markers or radiographic findings. Some laboratory obtained results which the clinician may observe to check for any response to therapy include normalization of tests such as white blood cell count, red blood cell count, platelet count, erythrocyte sedimentation rate, and various enzyme levels. Additionally, the clinician may observe a decrease in a detectable tumour marker(s). Alternatively, other tests can be used to evaluate objective improvement such as sonograms, nuclear magnetic resonance testing and positron emissions testing.

"Inhibiting the growth of tumour cells" can be evaluated by any accepted method of measuring whether growth of the tumour cells has been slowed or diminished. This includes direct observation and indirect evaluation such as subjective symptoms or objective signs as discussed above.

Accordingly, the compositions of the invention are administered to cells. Herein what is meant by "administered" is the administration of a therapeutically effective dose of the candidate agents of the invention to a cell either in cell culture or in a patient. Herein what is meant by "therapeutically effective dose" is a dose that produces the effects for which it is administered. The exact dose will depend on the purpose of the treatment, and will be ascertainable by one skilled in the art using known techniques. As is known in the art, adjustments for systemic versus localized delivery, age, body weight, general health, sex, diet, time of administration, drug interaction and the severity of the condition may be necessary, and will be ascertainable with routine experimentation by those skilled in the art. Herein what is meant by "cells" is almost any cell in which mitosis or meiosis can be altered.

Therefore, the present invention relates to the use of proline or proline derivatives or their salts, esters, isomers or prodrugs and anti-cancer ligands (preferably antibodies) for the manufacturing of a pharmaceutical composition for the treatment of a cell proliferative disorder. The pharmaceutical composition of the invention optionally comprises of one or more pharmaceutically acceptable adjuvants, excipients, carriers, buffers, diluents and/or customary pharmaceutical auxiliary substances. The combination-composition of the invention is administered in a pharmaceutically acceptable formulation. The present invention pertains to any pharmaceutically acceptable formulations, such as synthetic or natural polymers in the form of macromolecular complexes, nanocapsules, microspheres, or beads, and lipid-based formulations including oil-in-water emulsions, micelles, mixed micelles, synthetic membrane vesicles, and resealed erythrocytes. In addition to the said composition and the pharmaceutically acceptable polymer, the pharmaceutically acceptable formulation used in the method of the invention can comprise additional pharmaceutically acceptable carriers and/or excipients. As used herein, a pharmaceutically acceptable carrier includes any and all solvents, dispersion media, coatings, antibacterial and anti fungal agents, isotonic and absorption delaying agents, and the like that are physiologically compatible. For example, the carrier can be suitable for injection into the blood. Excipients include pharmaceutically acceptable stabilizers and disintegrants. In another embodiment, the pharmaceutically acceptable formulations comprise lipid-based formulations. Any of the known lipid-based drug delivery systems can be used in the practice of the invention. For instance, multivesicular liposomes (MVL), multilamellar liposomes (also known as multilamellar vesicles or MLV), unilamellar liposomes, including small unilamellar liposomes (also known as unilamellar vesicles or SUV) and large unilamellar liposomes (also known as large unilamellar vesicles or LUV), can all be used so long as a sustained release rate of the encapsulated combination-composition of the invention can be established. In one embodiment, the lipid-based formulation can be a multivesicular liposome system. The composition of the synthetic membrane vesicle is usually a combination of phospholipids, usually in combination with steroids, especially cholesterol. Other phospholipids or other lipids may also be used. Examples of lipids useful in synthetic membrane vesicle production include phosphatidylglycerols, phosphatidylcholines, phosphatidylserines, phosphatidyl-ethanolaminos, sphingolipids, cerebrosides, and gangliosides. Preferably phospholipids including egg phosphatidylcholine, dipalmitoylphosphatidylcholine, distearoylphosphatidylcholine, dioleoylphosphatidylcholine, dipalmitoylphosphatidylglycerol, and dioleoylphosphatidylglycerol are used. In another embodiment, the composition containing the combination-composition of the invention may be incorporated or impregnated into a bioabsorbable matrix. In addition, the matrix may be comprised of the said biopolymer. A suitable biopolymer for the present invention can include also one or more macromolecules selected from the group consisting of collagen, elastin, fibronectin, vitronectin, laminin, polyglycolic acid, hyaluronic acid, chondroitin sulphate, dermatan sulphate, heparin sulphate, heparin, fibrin, cellulose, gelatine, polylysine, echinonectin, entactin, thrombospondin, uvomorulin, biglycan, decorin, and dextran. The formulation of these macromolecules into a biopolymer is well known in the art. In a preferred embodiment, the therapeutic composition is not immunogenic when administered to a human patient for therapeutic purposes.

The therapeutic composition of the present invention can include pharmaceutically acceptable salts of the components therein. Pharmaceutically acceptable salts include the acid addition salts that are formed with inorganic acids such as hydrochloric or phosphoric acids, or such organic acids as acetic, tartaric, mandelic and the like. Salts formed with the free carboxyl groups of the proline and the proline derivatives can also be derived from inorganic bases such as sodium, potassium, ammonium, calcium or ferric hydroxides, and such organic bases as isopropylamine, trimethylamino, 2-ethylamino ethanol, histidine, procaine and the like. Physiologically tolerable carriers are well known in the art. Exemplary liquid carriers are sterile aqueous solutions which contain no materials in addition to the active ingredients and water, or contain a buffer such as sodium phosphate at a physiological pH value, in a physiological amount of saline or both, for example phosphate-buffered saline. Further still, aqueous carriers can contain more than one buffer salt, as well as salts such as sodium and potassium chlorides, dextrose, propylene glycol, polyethylene glycol and other solutes. Liquid compositions can also contain liquid phases in addition to and to the exclusion of water. Exemplary examples of such additional liquid phases include glycerine, vegetable oils such as cottonseed oil, organic esters such as ethyl oleate, and water-oil emulsions. A therapeutic composition contains a composition of the present invention, typically an amount of at least 0.1 weight percent of composition per weight of total therapeutic composition. A weight percent is a ratio by weight of composition of the invention to total composition. Thus, for example, 0.1 weight percent is 0.1 grams of proline, isomers, salts and fragments thereof together with the anti-cancer ligand per 100 grams of total composition.

The term "pharmaceutically acceptable salt" refers to those salts of compounds which retain the biological effectiveness and properties of the free bases and which are obtained by reaction with inorganic acids such as hydrochloric acid, hydrobromic acid, sulphuric acid, nitric acid, phosphoric acid, methanesulphonic acid, ethanesulphonic acid, ptoluenesulphonic acid, salicylic acid and the like. Pharmaceutically acceptable salts include alkali metal salts, such as sodium and potassium, alkaline earth salts and ammonium salts.

The pharmaceutical composition containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch, or alginic acid; binding agents, for example starch, gelatine or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874, to form osmotic therapeutic tablets for control release. A pharmaceutical composition may also, or alternatively, contain one or more drugs, which may be linked to a modulating agent or may be free within the composition. Virtually any drug may be administered in combination with a modulating agent as described herein, for a variety of purposes as described below. Examples of types of drugs that may be administered with a modulating agent include analgesics, anaesthetics, antianginals, antifungals, antibiotics, anti-cancer drugs (e.g., taxol or mitomycin C), anti-inflammatories (e.g., ibuprofen and indomethacin), anthelmintics, antidepressants, antidotes, antiemetics, antihistamines, antihypertensives, antimalarials, antimicrotubule agents (e.g., colchicine or vinca alkaloids), antimigraine agents, antimicrobials, antiphsychotics, antipyretics, antiseptics, anti-signalling agents (e.g., protein kinase C inhibitors or inhibitors of intracellular calcium mobilization), antiarthritics, antithrombin agents, antituberculotics, antitussives, antivirals, appetite suppressants, cardioactive drugs, chemical dependency drugs, cathartics, chemotherapeutic agents, coronary, cerebral or peripheral vasodilators, contraceptive agents, depressants, diuretics, expectorants, growth factors, hormonal agents, hypnotics, immunosuppression agents, narcotic antagonists, parasympathomimetics, sedatives, stimulants, sympathomimetics, toxins (e.g., cholera toxin), tranquilizers and urinary anti-infectives.

Formulations for oral use may also be presented as hard gelatine capsules where in the active ingredient is mixed with an inert solid diluent, for example calcium carbonate, calcium phosphate or kaolin, or as soft gelatine capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate polyvinylpyrrolidone, gum tragacanth and gum acacia; dispersing or wetting agents may be a naturally occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such a polyoxyethylene with partial esters derived from fatty acids and hexitol anhydrides, for example polyoxyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified, for example sweetening, flavouring and colouring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soya bean, lecithin, and esters/partial esters derived from fatty acids and hexitol anhydrides, for example sorbitan monooleate and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain demulcent, preservatives, flavouring agents and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be in a sterile injectable solution or suspension in a non-toxic parenterally-acceptable diluent or solvent, for example as absolution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

For administration to patients, the active substances of the present invention are mixed with a pharmaceutically acceptable carrier or diluent in accordance with routine procedures. Therapeutic formulations will be administered by intravenous infusion or by subcutaneous injection. The formulations can also contain, if desired, other therapeutic agents.

Dosage levels of the order of from about 0.05 mg to about 140 mg per kilogram of body weight per: day are useful in the treatment of the above-indicated conditions (about 2.5 mg to about 7 g per patient per day). For example, inflammation may be effectively treated by the administration of from about 0.01 to 50 mg of the compound per kilogram of body weight per day (about 0.5 mg to about 3.5 g per patient per day). The amount of active ingredient that may be combined with the carrier materials to produce a single dosage form will vary depending upon the host treated and the particular mode of administration. For example, a formulation intended for the oral administration of humans may vary from about 5 to about 95% of the total composition. Dosage unit forms will generally contain between from about 1 mg to about 500 mg of active ingredient. It will be understood, however, that the specific dose level for any particular patient will depend upon a variety of factors including the activity of the specific compound employed, the age, body weight, general health, sex, diet time of administration, route of administration, rate of excretion, drug combination and the severity of the particular disease undergoing therapy. The dose effective amount of compounds according to the invention will vary depending upon factors including the particular compound, toxicity, and inhibitory activity, the condition treated, and whether the compound is administered alone or with other therapies. Typically a dose effective amount will range from about 0.0001 mg/kg to 1500 mg/kg, more preferably 1 to 1000 mg/kg, more preferably from about 1 to 150 mg/kg of body weight, and most preferably about 50 to 100 mg/kg of body weight. The invention relates also to a process or a method for the treatment of the abovementioned pathological conditions. The compounds of the present invention can be administered prophylactically or therapeutically, preferably in an amount that is effective against the mentioned disorders, to a warm-blooded animal, for example a human, requiring such treatment, the compounds preferably being used in the form of pharmaceutical compositions.

Formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, and intramuscular administration and formulation.

A. Oral Delivery

In certain applications, the pharmaceutical compositions disclosed herein may be delivered via oral administration. As such, these compositions may be formulated with an inert diluent or with an assimilable edible carrier, or they may be enclosed in hard- or soft-shell gelatine capsule, or they may be compressed into tablets, or they may be incorporated directly with the food of the diet.

The active compounds may even be incorporated with excipients and used in the form of ingestible tablets, buccal tables, troches, capsules, elixirs, suspensions, syrups, wafers, and the like. The tablets, troches, pills, capsules and the like may also contain the following: a binder, as gum tragacanth, acacia, cornstarch, or gelatine; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavouring agent, such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. A syrup of elixir may contain the active compound sucrose as a sweetening agent, methyl and propylparabens as preservatives, a dye and a flavouring, such as cherry or orange flavour. Of course, any material used in preparing any dosage unit form should be pharmaceutically pure and substantially non-toxic in the amounts employed. In addition, the active compounds may be incorporated into sustained-release preparation and formulations.

Typically, these formulations contain at least 0.1% of the active compound of the invention or more, although the percentage of the active ingredient(s) may, of course, be varied and may conveniently be between about 1 or 2% and about 60% or 70% or more of the weight or volume of the total formulation. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerine and potassium bicarbonate, or dispersed in a dentifrice, or added in a therapeutically-effective amount to a composition that may include water, binders, abrasives, flavouring agents, foaming agents, and humectants. Alternatively the compositions may be fashioned into a tablet or solution form that may be placed under the tongue or otherwise dissolved in the mouth.

B. Injectable Delivery

In certain circumstances it will be desirable to deliver the pharmaceutical compositions disclosed herein parenterally, intravenously, intramuscularly, or even intraperitoneally. Solutions of the active compounds as free bases or as pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatine.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion. Some necessary variation in the dosage will occur depending on the condition of the subject being treated. The person responsible for administration will, in any event, determine the appropriate dose for the individual subject. Moreover, for human administration, preparations should meet sterility, pyrogenicity, and the general safety and purity standards as required by national or regional offices of biologics standards.

Sterile injectable solutions are prepared by incorporating the active compounds in the required amount in the appropriate solvent with various ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

c. Nasal Delivery

In certain embodiments, the pharmaceutical compositions may be delivered by intranasal sprays, inhalation, and/or other aerosol delivery vehicles. Likewise, the delivery of drugs using intranasal microparticle resins and lysophosphatidylglycerol compounds are also well-known in the pharmaceutical arts.

D. Liposome-, Nanocapsule-, and Microparticle-mediated Delivery

In certain embodiments, the inventors contemplate the use of liposomes, nanocapsules, microparticles, microspheres, lipid particles, vesicles, and the like, for the introduction of the compositions of the present invention into suitable host cells. In particular, the compositions of the present invention may be formulated for delivery either encapsulated in a lipid particle, a liposome, a vesicle, a nanosphere, or a nanoparticle or the like.

Such formulations may be preferred for the introduction of pharmaceutically-acceptable formulations of the combination-composition or constructs disclosed herein. The formation and use of liposomes is generally known to those of skill in the art. Recently, liposomes were developed with improved serum stability and circulation half-times (Gabizon and Papahadjopoulos, 1988). Further, various methods of liposome and liposome like preparations as potential drug carriers have been reviewed (Takakura, 1998; Chandran et al., 1997; Margalit, 1995; U.S. Pat. Nos. 5,567,434; 5,552,157; 5,565,213; 5,738,868 and 5,795,587, each specifically incorporated herein by reference in its entirety). In addition to liposome characteristics, an important determinant in entrapping compounds is the physicochemical properties of the compound itself. Polar compounds are trapped in the aqueous spaces and nonpolar compounds bind to the lipid bilayer of the vesicle. Polar compounds are released through permeation or when the bilayer is broken, but nonpolar compounds remain affiliated with the bilayer unless it is disrupted by temperature or exposure to lipoproteins. Both types show maximum efflux rates at the phase transition temperature. Liposomes interact with cells via four different mechanisms: endocytosis by phagocytic cells of the reticuloendothelial system such as macrophages and neutrophils; adsorption to the cell surface, either by non-specific weak hydrophobic or electrostatic forces, or by specific interactions with cell-surface components; fusion with the plasma cell membrane by insertion of the lipid bilayer of the liposome into the plasma membrane with simultaneous release of liposomal contents into the cytoplasm; and by transfer of liposomal lipids to cellular or subcellular membranes, or vice versa, without any association of the liposome contents. It often is difficult to determine which mechanism is operative and more than one may operate at the same time.

The fate and disposition of intravenously injected liposomes depend on their physical properties, such as size, fluidity, and surface charge. They may persist in tissues for hours or days, depending on their composition, and half lives in the blood range from minutes to several hours. Larger liposomes, such as MLVs and LUVs, are taken up rapidly by phagocytic cells of the reticuloendothelial system, but physiology of the circulatory system restrains the exit of such large species at most sites. They can exit only in places where large openings or pores exist in the capillary endothelium, such as the sinusoids of the liver or spleen. Thus, these organs are the predominate site of uptake. On the other hand, SUVs show a broader tissue distribution but still are sequestered highly in the liver and spleen. In general, this in vivo behaviour limits the potential targeting of liposomes to only those organs and tissues accessible to their large size. These include the blood, liver, spleen, bone marrow, and lymphoid organs.

Targeting is generally not a limitation in terms of the present invention. However, should specific targeting be desired, methods are available for this to be accomplished. Antibodies may be used to bind to the liposome surface and to direct the antibody and its drug contents to specific antigenic receptors located on a particular cell-type surface. Carbohydrate determinants (glycoprotein or glycolipid cell-surface components that play a role in cell-cell recognition, interaction and adhesion) may also be used as recognition sites as they have potential in directing liposomes to particular cell types. Mostly, it is contemplated that intravenous injection of liposomal preparations would be used, but other routes of administration are also conceivable.

Alternatively, the invention provides for pharmaceutically-acceptable nanocapsule formulations of the compositions of the present invention. Nanocapsules can generally entrap compounds in a stable and reproducible way (Henry-Michelland et al., 1987; Quintanar-Guerrero et al., 1998; Douglas et al., 1987). To avoid side effects due to intracellular polymeric overloading, such ultra fine particles (sized around 0.1 .mu.m) should be designed using polymers able to be degraded in vivo. Biodegradable polyalkyl-cyanoacrylate nanoparticles that meet these requirements are contemplated for use in the present invention.

The subjects treated will typically comprise of mammals and will preferably be human subjects, e.g., human cancer subjects. The compounds of the invention may be used alone or in combination. Additionally, the treated compounds may be utilized with other types of treatments, e.g., cancer treatments. For example, the subject compounds may be used with other chemotherapies, e.g., tamoxifen, taxol, methothrexate, biologicals, such as antibodies, growth factors, lymphokines, or radiation, etc. Combination therapies may result in synergistic results. The preferred indication is cancer, especially the cancers identified previously.

The compositions and methods provided herein are particularly deemed useful for the treatment of cancer including solid tumours such as skin, breast, brain, cervical carcinomas, testicular carcinomas, etc. More particularly, cancers that may be treated by the compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesotheliorna; Gastrointestinal: oesophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumours, vipoma), small bowel (adenocarcinoma, lymphoma, carcinoid tumours, Karposi's sarcoma, leiomyoma, haemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumour [nephroblastoma], lymphoma, leukaemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumours, lipoma); Liver: hepatoma (hepatocellular carcinoma), cholangiocarcinoma, hepatoblastoma, angiosarcoma, hepatocellular adenoma, haemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumour chordoma, osteochronfroma (osteocartilaginous exostoses), benign chondroma, chondroblastoma, chondromyxofibroma, osteoid osteoma and giant cell tumours; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumours), spinal cord neurofibroma, meningioma, glioma, sarcoma); Gynaecological: uterus (endometrial carcinoma), cervix (cervical carcinoma, pre-tumour cervical dysplasia), ovaries (ovarian carcinoma [serous cystadenocarcinorna, mucinous cystadenocarcinoma, unclassified carcinoma], granulosa-thecal cell tumours, Sertoli-Leydig cell tumours, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above identified conditions.

Therefore, as used herein, "cancer" refers to all types of cancer or neoplasm or malignant tumours found in mammals, including carcinomas and sarcomas. Examples of cancers are cancer of the brain, breast, cervix, colon, head & neck, kidney, lung, non-small cell lung, melanoma, mesothelioma, ovary, sarcoma, stomach, uterus and Medulloblastoma.

The term "leukaemia" refers broadly to progressive, malignant diseases of the blood-forming organs and is generally characterized by a distorted proliferation and development of leukocytes and their precursors in the blood and bone marrow. Leukaemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukaemic or aleukaemic (subleukaemic). The P388 leukaemia model is widely accepted as being predictive of in vivo anti-leukaemic activity. It is believed that compound that tests positive in the P388 assay will generally exhibit some level of anti-leukaemic activity in vivo regardless of the type of leukaemia being treated. Accordingly, the present invention includes a method of treating leukaemia, and, preferably, a method of treating acute nonlymphocytic leukaemia, chronic lymphocytic leukaemia, acute granulocytic leukaemia, chronic granulocytic leukaemia, acute promyelocytic leukaemia, adult T-cell leukaemia, aleukaemic leukaemia, a leukocythemic leukaemia, basophylic leukaemia, blast cell leukaemia, bovine leukaemia, chronic myelocytic leukaemia, leukaemia cutis, embryonal leukaemia, eosinophilic leukaemia, Gross' leukaemia, hairy-cell leukaemia, hemoblastic leukaemia, hemocytoblastic leukaemia, histiocytic leukaemia, stem cell leukaemia, acute monocytic leukaemia, leukopenic leukaemia, lymphatic leukaemia, lymphoblastic leukaemia, lymphocytic leukaemia, lymphogenous leukaemia, lymphoid leukaemia, lymphosarcoma cell leukaemia, mast cell leukaemia, megakaryocytic leukaemia, micromyeloblastic leukaemia, monocytic leukaemia, myeloblastic leukaemia, myelocytic leukaemia, myeloid granulocytic leukaemia, myelomonocytic leukaemia, Naegeli leukaemia, plasma cell leukaemia, plasmacytic leukaemia, promyelocytic leukaemia, Rieder cell leukaemia, Schilling's leukaemia, stem cell leukaemia, subleukaemic leukaemia, and undifferentiated cell leukaemia.

The term "sarcoma" generally refers to a tumour which is made up of a substance like the embryonic connective tissue and is generally composed of closely packed cells embedded in a fibrillar or homogeneous substance. Sarcomas which can be treated with combination-composition of the invention and optionally a potentiator and/or chemotherapeutic agent include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumour sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumour arising from the melanocytic system of the skin and other organs. Melanomas which can be treated with said combination-compositions and optionally a potentiator and/or another chemotherapeutic agent include acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

The term "carcinoma" refers to a malignant new growth made up of epithelial cells tending to infiltrate the surrounding tissues and give rise to metastases. Exemplary carcinomas which can be treated with said combination-compositions and optionally a potentiator and/or a chemotherapeutic agent include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epithelial adenoids, exophytic carcinoma, carcinoma ex ulcer, carcinoma fibrosum, gelatiniformi carcinoma, gelatinous carcinoma, giant cell carcinoma, carcinoma gigantocellulare, glandular carcinoma, granulosa cell carcinoma, hair-matrix carcinoma, haematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullar, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, pre-invasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

Additional cancers which can be treated with the composition according to the invention include, for example, Hodgkin's Disease, Non-Hodgkin's Lymphoma, multiple mycloma, neuroblastoma, breast cancer, ovarian cancer, lung cancer, rhabdomyosarcoma, primary thrombocytosis, primary macroglobulinemia, small-cell lung tumours, primary brain tumours, stomach cancer, colon cancer, malignant pancreatic insulanoma, malignant carcinoid, unary bladder cancer, pre-malignant skin lesions, testicular cancer, lymphomas, thyroid cancer, neuroblastoma, oesophageal cancer, genitourinary tract cancer, malignant hypercalcaemia, cervical cancer, endometrial cancer, adrenal cortical cancer, and prostate cancer.

The present invention concerns the use of proline or proline derivatives or their salts, esters, isomers or prodrugs to increase and/or optimise the binding of anti-cancer antibodies to the tumour antigens and/or cell receptors. Therefore a method of improving target selectivity of antibodies, wherein the target is treated in vitro or in vivo with the combination composition of the invention or with proline, proline derivatives or their salts, esters, isomers or prodrugs, is also an object of the present invention.

The agents described in the present invention are believed to have the following objectives:

Optimisation of the cell receptors for antibodies binding to the tumour antigens.

Promotion/increase of the cell cycle progressions inhibition.

Acceleration of the terminal differentiation or apoptosis of the cells.

Reduction of the antibody-dependent cellular cytotoxicity (ADCC).

Activation of the tyrosine kinase inhibitors.

Increase of the sensitivity of tumour cells to cytokines such as tumour necrosis factor.

Increase of the anti-tumour response of antibodies and/or chemotherapeutics and/or anti-tumour agents in patients. This will result in the achievement of higher therapeutic efficacy of the antibodies and/or chemotherapeutics and/or anti-tumour agents and the decrease of the adverse events and the improvement of the quality of life of the patients.

The summary of the description contained herein includes numerous terms which are understood by those of ordinary skill, taking into account the following definitions:

The term "antibodies" refers to the proteins produced by cells of the immune system which attach to certain chemicals that the body recognises as not being part of its own normal tissues. Antibodies help the body to resist infections and even cancer.

Monoclonal antibodies (mAbs) are a special type of antibody that can be mass-produced in laboratories. Trastuzumab (Herceptin) is the first monoclonal antibody drug used to treat women with breast cancer. It works by preventing the HER2/neu protein from promoting excessive growth of breast cancer cells and may also help the immune system fight the cancer.

Other monoclonal antibodies that recognise the HER2/neu protein are being tested in clinical trials as are monoclonal antibodies that block other growth-promoting molecules of breast cancer cells. Monoclonal antibodies that have been designed to guide immune system cells, chemotherapy drugs, or radiation therapy directly to the tumour are also being tested.

Monoclonal antibodies bind to specific proteins which are found on the surface of human cells and play a role in the cell growth regulation, e.g. Herceptin binds to a protein called HER2. In laboratory experiments, Herceptin inhibited tumour cell growth by this binding action. In the case of metastatic breast cancer cells, approximately 80% of the tumours produce excess amounts of HER2.

The antibodies can be used either alone to kill cancer cells, or as carriers of other substances used also for treatment of diagnostic purposes. For example, chemotherapeutic agents can be attached to monoclonal antibodies to deliver high concentrations of these toxic substances directly to the tumour cells. In theory, this approach is less toxic and more effective than conventional chemotherapy because it reduces the delivery of harmful agents to normal tissues.

During the diagnostic process, monoclonal antibodies may be used to carry radioactive substances to cancer cells within the body, thus pinpointing the location of metastases that were previously undetected by other methods.

The potential side effects of monoclonal antibodies may include dyspnoea (shortness of breathe) and mild wheezing, fever, headache, rash, nausea and vomiting, tachycardia (rapid heartbeat) and/or allergic reactions.

All chemotherapeutics including cisplatin, carboplatin, taxol, 5FU etc, are highly toxic and generally poorly tolerated. The potential side effects of chemotherapeutics may include haematologic toxicities such as thrombocytopenia, leucopoenia and anaemia, nonhaematologic toxicities such as nephrotoxicity, ototoxicity, neurotoxicity and emesis, injection site complications, sepsis, cardiovascular effects such as hypotension and bradycardia, diarrhoea, mucositis, dermatologic effects such as alopecia, respiratory effects such as interstitial pneumonia, lung fibrosis and pulmonary embolism, metabolic/nutritional effects such as weight loss, peripheral oedema and/or dehydration.

The key concepts of the invention can be summarised as follows:

The present invention concerns the use of proline or proline derivatives or their salts, esters, isomers or prodrugs to increase and/or optimise the binding of the antibodies to the tumour antigens and/or cell receptors.

Therefore a method of improving target selectivity of antibodies wherein the target is treated in vitro or in vivo with the combination composition of the invention or with proline or proline derivatives or their salts, esters, isomers or prodrugs is also an object of the present invention.

The main objective and advantage of the use of the combination-composition, the compounds of the present patent and the method of treatment is to reduce the administered amount of the antibody, and/or to increase the therapeutic efficacy of the administered antibody and anti-tumour agents, and/or to reduce the toxic side effects of the administered antibody and which will result in the increase and improvement of the quality of life of the treated cancer patients.

The following summary will explain the possible different functions and mode of action of the extracellular signalling molecules/cell surface receptors, the antibodies and the proline derivatives involved in the complex effect.

Extracellular Signalling Molecules/Cell Surface Receptors

Extracellular signalling molecules are synthesized and released by signalling cells and produce a specific response only in target cells that have receptors for the signalling molecules. In multicellular organisms, an enormous variety of chemicals, including small molecules (e.g. amino acid or lipid derivatives, acetylcholine), peptides and proteins are used in this type of cell-to-cell communication.

The seven major classes of cell surface receptors are:
Protein-coupled receptors
Cytokine receptors
Receptors Tyrosine kinases
TGF receptors
Hedgehog (Hg) receptors
Wnt receptors
Notch receptors Extracellular signalling molecules regulate interactions between unicellular organisms and are critical regulators of physiology and development in multicellular organisms.

Binding of extracellular signalling molecules to cell-surface receptors triggers intracellular signal-transduction pathways that ultimately modulate cellular metabolism, function or gene expression.

External signals include membrane-anchored and secreted proteins and peptides, small lipophilic molecules (e.g. steroid hormones, thyroxine), small hydrophilic molecules derived from amino acids (e.g. epinephrine), gases (e.g. nitric oxide), and physical stimuli (e.g. light).

Signals from one cell can act on nearby cells (paracrine), on distant cells (endocrine), or on the signalling cell itself (autocrine).

Receptors bind ligands with considerable specificity, which is determined by non-covalent interactions between a ligand and specific amino acids in the receptor protein.

The maximal response of a cell to a particular ligand generally occurs at ligand concentrations at which most of its receptors are still not occupied Communication by extracellular signals usually involves the following steps: (1) synthesis and (2) release of the signalling molecule by the signalling cell; (3) transport of the signal to the target cell; (4) binding of the signal by a specific receptor protein, leading to its activation; (5) initiation of one or more intracellular signal-transduction pathways by the activated receptor; (6) specific changes in cellular function, metabolism and development; and (7) removal of the signal, which often terminates the cellular response. The vast majority of receptors are activated by binding of secreted or membrane-bound molecules (e.g. hormones, growth factors, neurotransmitters and pheromones). Some receptors however, are activated by changes in the concentration of a metabolite (e.g. oxygen or nutrients) or by physical stimuli (e.g. light, touch, heat).

mAbs, bs-Abs and Polyclonal Antibodies

The proline, proline derivatives and their salts, esters, isomers and prodrugs optimise and/or improve the target selectivity of the mAbs to the cell receptors. These antibodies, like the normal ones, are structurally complex multifunctional macromolecules. Some, but not all, of their activities depend on the complementarity-determining regions within the specific antigen-binding site.

When directed against signalling molecules, such as CD20, c-erbB-2/HER-2 and EGFR, mAbs can be shown to exhibit either agonistic or antagonistic behaviour. In other words, they can be shown to "remove" and/or to "switch off" their target antigen, resulting in anti-proliferative effects.

Thus even, considering the direct effect of mAbs, it is clear that there is a multiplicity of possible responses determined by the properties of the antigen, the antibody and the cellular context.

Patients' individual responses are the sum of multiple factors including expression of the target antigen (and other signalling molecules that might compensate if the former is inactivated), levels of circulating Ig (immunoglobulin) or immune complexes and the functional status of their effector cells.

Host immune responses can also be induced by the use of bispecific antibodies (bs-Abs) on which one Fab arm recognises the tumour antigen and the other engages epitopes on T cells (CD3) or specific FcyR.

Even when tumours are pre-selected to be antigen positive, only a minority of patients respond to a therapy involving mAbs.

Proline Derivatives

Cis-4-hydroxy-L-proline (CHP) is a human endogenous compound with unknown physiological functions. The trans-isomer of CHP is present in high concentrations in collagen and elastin, and therefore is vital for connective tissue synthesis and structure. Endogenous concentrations of CHP have been determined in plasma and urine samples collected from healthy volunteers and cancer patients. Cancer patients treated with high doses of oral CHP have shown high concentrations of CHP and trans-4-hydroxy-L-proline (THP) in blood plasma. The results indicate that CHP and THP may have a relevant physiological role, which is not yet elucidated.

Based on the concepts mentioned above which discuss the extracellular signalling molecules, cell surface receptors and the mAbs, bs-mAbs and polyclonal antibodies and based on the results represented below, it was surprisingly found that CHP, 4-hydroxy-1-methyl-proline, 1-methyl-4-phenylamino-carbonyloxy-proline and other proline derivatives described above (which are the proline derivatives included in the present inventions idea and claims), may effect the cellular change, modification, generation and/or normalisation of the cell and/or may improve the agglutination behaviours of the tumour cells in a specific manner which may surprisingly result in an increase in the efficacy of the mAbs, and/or bispecific antibodies (bs-Abs) and/or other antibodies in targeting the specific tumour antigens such as EGFR's.

Proline, or proline derivatives or their salts, esters, isoforms or prodrugs can be administered in different schemes (prior, simultaneously or post) treatment with antibodies and/or pharmacological agents, drugs and any ingredients. The agents described in the invention could be administered in any pharmaceutical formulation, e.g. infusion, injection, intramuscular, subcutaneous, etc.

The following examples illustrate the results of the experiments to investigate the influence of proline derivatives on the activities and effects of the antibodies.

These examples are not limited to the use of the combination composition and the compound and/or method of treatment in this present patent.

EXAMPLES

1. Introduction

Cis-4-hydroxy-1-proline (CHP) and a number of its derivatives have been investigated in combination with Cetuximab, Rituximab, Avastatin and specific EGFR-Antibodies against a panel of cancer cell lines.

MTT proliferation tests were performed as described. The proliferation control of both the untreated cells and the CHP pre-treated cells is set to 100%.

All antibodies were used as supplied for clinical use. The preparations were used in dilutions of >50 fold.

2. Materials and Methods

2.1 Cell Lines

Unless otherwise indicated, all cell lines were obtained from the American Type Culture Collection (ATCC, Rockville, Md.) and grown to confluent monolayers in RPMI-1640 bicarbonate medium (Seromed, Berlin, Germany) in a humidified incubator (5% $CO_2$, 37° C.). Cells were checked for mycoplasma contamination. The medium was supplemented with 10% heat-inactivated foetal bovine serum (Seromed) and 4 mM glutamine. The cells were subcultured by trypsination (0.03% trypsin containing 0.02% EDTA, three times a week). Cells numbers were counted using a TOA Sysmex microcellcounter (TOA, Tokyo, Japan).

2.2 Chemicals and Solutions

Unless otherwise indicated, all chemicals were obtained from Sigma (St. Louis, Mo.). Compounds to be tested were used as supplied. CHP, its derivatives and the antibodies have been used in concentrations indicated in the different examples.

2.3 Chemosensitivity Assays $10^4$ cells/well were distributed into 96-well microtitre plates (100 µl medium) and the compounds to be tested were added in another 100 µl volume. All compounds were diluted in triplicate or in most cases in quadruplicate. Plates were incubated under tissue culture conditions for 4 days, except those for tests investigating the relationship between application time and response, and cell viability was measured using a modified MTT assay (formazane dye formation from tetrazolium salts by mitochondrial reduction; EZ4U, Biomedica, Vienna, Austria), assessing mitochondrial activity and thereby cell viability/cell numbers. In brief, the supplied substrate was diluted in an activator solution and 20 µl of the mixture added per well for 2 hrs. The optical density was measured at 450 nm using an empty well as reference in a microplate reader (Eurogenetics, Brussels, Belgium). For each cell line, 8 wells were used to measure the MTT signal of the medium control without test substances and the proliferation in the test wells was calculated in relation to these control values set to 100%. Test results were recorded between 0.3 and 1.5 optical densities for slowly and rapidly proliferating cells respectively.

Example 1

Cetuximab and the Proliferation Activities of the Cell Lines A431 and SW620

A431 epidermoid carcinoma exhibits a pronounced overexpression of the epidermal growth factor receptor (EGFR; in our experiments approximately 20× fold compared to the EGFR-positive colon cancer cell lines). SW620chp4 and A431chp4 cells represent cells pre-treated with 400 µg/ml CHP for 5 days under tissue culture conditions. (con=untreated control; *=significantly different).

Example 1.1

| SW620con | SW620chp4 | Cetuximab (µg/ml) |
|---|---|---|
| 100.5 ± 4.3 | 98.5 ± 3.2 | 50 |
| 101.7 ± 2.7 | 99.2 ± 2.9 | 25 |
| 100.2 ± 4.0 | 98.6 ± 2.6 | 12.5 |
| 102.7 ± 1.8 | 97.8 ± 4.1* | 6.3 |
| 101.8 ± 2.1 | 92.7 ± 0.6* | 3.2 |
| 101.5 ± 1.5 | 93.9 ± 2.1* | 1.6 |

Figure 1:
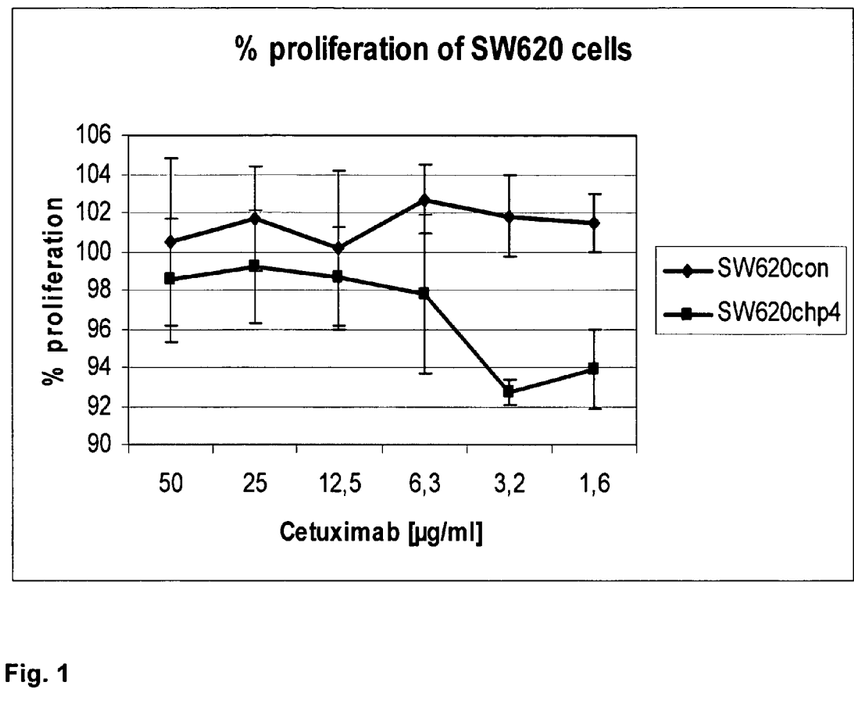
FIG. 1 depicts proliferation activities of SW620 cells (in %) treated with varying concentrations of Cetuximab after pretreatment with CHP in comparison to untreated control(s).

The results are depicted in FIG. 1.

Example 1.2

| A431con | A431chp4 | Cetuximab (µg/ml) |
|---|---|---|
| 92.3 ± 2.4 | 98.4 ± 4.6* | 50 |
| 94.7 ± 1.9 | 101.1 ± 2.8* | 25 |
| 89.3 ± 1.6 | 98.7 ± 3.8* | 12.5 |
| 91.3 ± 4.7 | 99.4 ± 1.5* | 6.3 |
| 93.3 ± 1.9 | 101.9 ± 3.4* | 3.2 |
| 89.5 ± 2.6 | 92.6 ± 9.1 | 1.6 |

*significantly different

Figure 2:
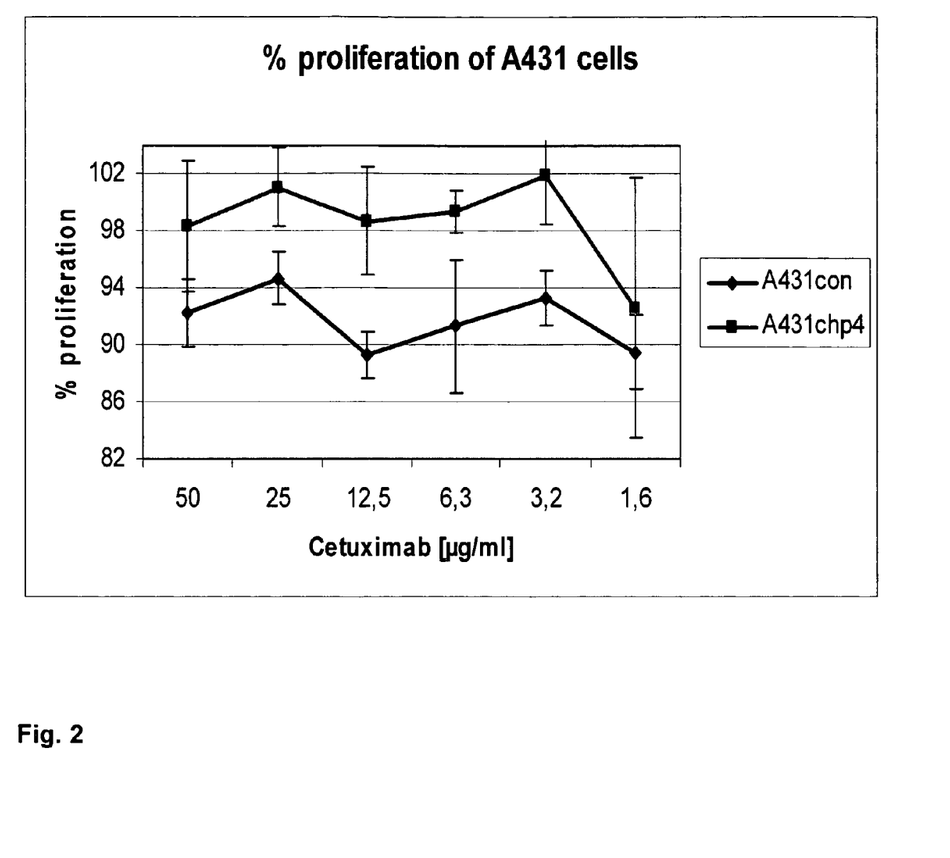
FIG. 2 depicts proliferation activities of A431 cells (in %) treated with varying concentrations of Cetuximab after pretreatment with CHP in comparison to untreated control(s).

The results are depicted in FIG. 2.

Conclusion

SW620 EGFR-low expressing cell line: pre-incubation with CHP surprisingly resulted in more inhibitory activity for Cetuximab at low concentrations (1.6-6.3 µg/ml).

A431 EGFR-overexpressing cell line: pre-incubation of A431 cells with CHP (which reduced expression of EGFR) surprisingly results in antagonistic interaction with Cetuximab.

High expression EGFR-Pre-incubation CHP→surprisingly reduces activity of Cetuximab Low expression of EGFR-Pre-incubation CHP→surprisingly causes enhancement of Cetuximab Example 2

Cetuximab and the Proliferation Activities of the Cell Lines Colo205 and SW620

Cetuximab was used at a fixed concentration of 40 µg/ml (C205cetu, SW620cetu) and CHP was varied from 400-6.3 µg/ml in direct combination for Colo205 colon cancer and SW620 colon cancer cells (con=untreated control, *=significantly different).

Example 2.1

| C205con | C205cetu | CHP |
|---|---|---|
| 9.9 ± 0.4 | 12.7 ± 1.5* | 400 |
| 15.7 ± 1.0 | 17.4 ± 0.7* | 200 |

-continued

| C205con | C205cetu | CHP |
|---|---|---|
| 45.5 ± 3.2 | 41.1 ± 0.8 | 100 |
| 84.2 ± 2.1 | 88.9 ± 2.2* | 50 |
| 94.4 ± 6.2 | 97.8 ± 7.3 | 25 |
| 92.2 ± 1.4 | 93.8 ± 3.6 | 12.5 |
| 99.4 ± 0.2 | 100.7 ± 2.1 | 6.3 |

Figure 3:
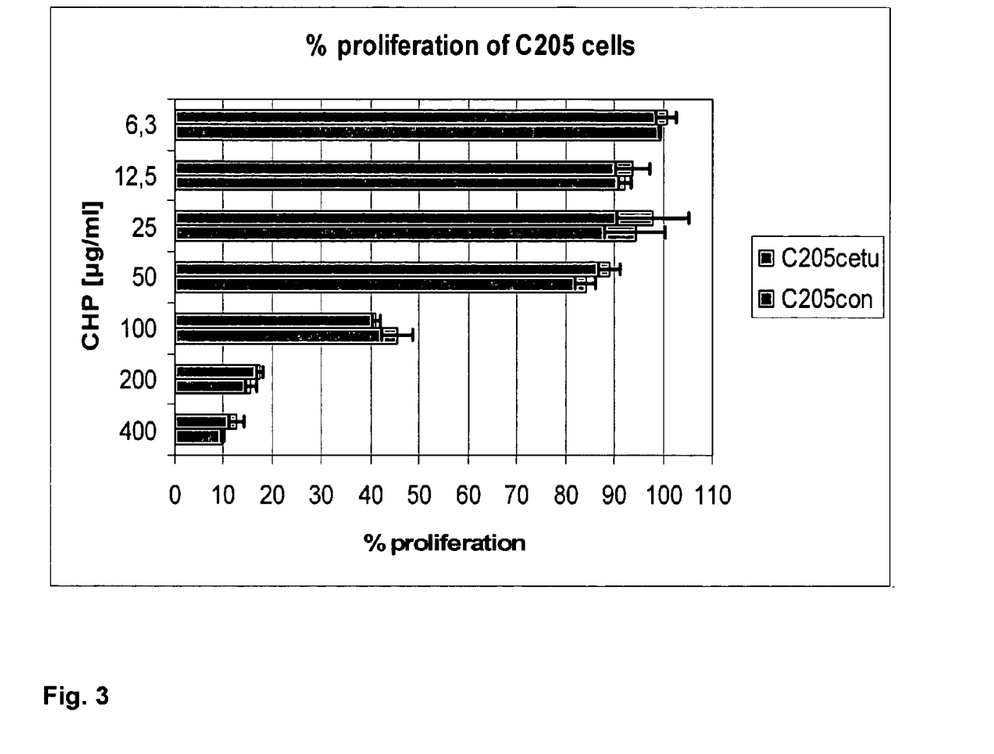
FIG. 3 shows proliferation activities of C205 cells (in %) treated with a direct combination of Cetuximab and CHP (the concentration of CHP was varied) in comparison to untreated control(s).

The results are depicted in FIG. 3.

Example 2.2

| SW620con | SW620cetu | CHP |
|---|---|---|
| 51.3 ± 3.7 | 49.3 ± 2.0 | 400 |
| 69.9 ± 2.6 | 67.8 ± 1.1 | 200 |
| 85.2 ± 0.7 | 86.1 ± 1.1 | 100 |
| 91.9 ± 4.1 | 98.8 ± 8.7* | 50 |
| 92.3 ± 0.9 | 98.7 ± 6.8* | 25 |
| 98.7 ± 3.0 | 110.1 ± 5.0* | 12.5 |
| 99.5 ± 0.4 | 104.5 ± 7.0* | 6.3 |

*significantly different

Figure 4:
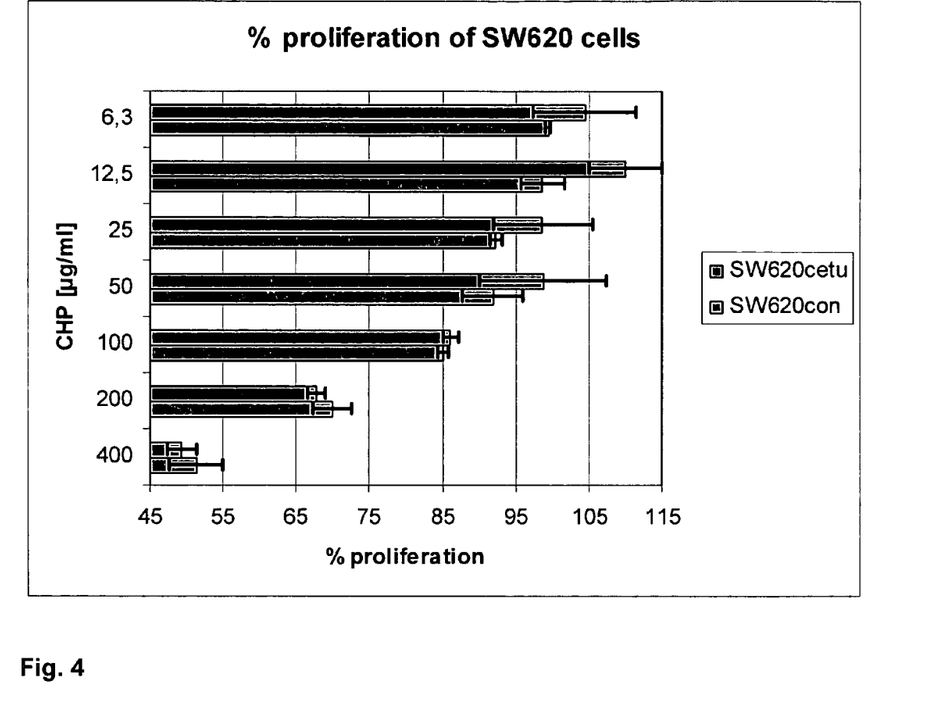
FIG. 4 shows the proliferation activities of SW620 cells (in %) treated with a direct combination of Cetuximab and CHP (the concentration of CHP was varied) in comparison to untreated control(s).

The results are depicted in FIG. 4.

Conclusion

CHP is surprisingly antagonistic with Cetuximab for Colo205 cells at higher concentrations of CHP (50, 200 and 400 µg/ml) and surprisingly antagonistic with Cetuximab for SW620 cells at low concentrations of CHP (6.3-50 µg/ml). Colo205 express significant amounts of EGFR at the cell surface, whereas SW620 seems to have very low expression of EGFR (data not shown).

Direct combination of CHP-Cetuximab surprisingly showed an antagonistic effect in the cell lines colo205 and SW620.

Example 3

Cetuximab and the Proliferation Activities of the Cell Lines HT29, WI38 and DLD1

CHP Pre-Treatment

Similar experiments were performed using more cell lines, namely HT29 colon cancer cells, WI38 normal fibroblasts and DLD1 colon cancer cells. Pre-treatment of the cells with 200 µg/ml CHP for 5 days and tests using Cetuximab dilutions ranging from 40-1.3 µg/ml.

(*=significantly different)

| HT29con | HT29chp2 | WI38con | WI38chp2 |
|---|---|---|---|
| 96.9 ± 1.1 | 101.6 ± 2.2* | 93.1 ± 1.8 | 110.5 ± 6.1* |
| 100.3 ± 2.4 | 102.5 ± 4.6 | 91.8 ± 3.8 | 118.8 ± 10.1** |
| 99.9 ± 1.8 | 103.5 ± 1.1 | 87.1 ± 5.0 | 125.6 ± 0.5* |
| 100.4 ± 4.4 | 104.5 ± 3.7 | 84.1 ± 0.5 | 116.0 ± 2.5* |
| 97.6 ± 8.8 | 106.1 ± 6.6 | 88.5 ± 2.0 | 117.9 ± 1.1* |
| 96.6 ± 7.3 | 90.1 ± 3.8 | 94.7 ± 0.9 | 116.5 ± 7.4* |

| DLD1con | | DLD1chp2 | |
|---|---|---|---|
| 93.4 ± 5.2 | | 103.3 ± 3.5* | |
| 99.8 ± 0.2 | | 108.7 ± 15.1* | |

-continued

| | |
|---|---|
| 98.1 ± 4.9 | 106.8 ± 7.1 |
| 109.3 ± 6.8 | 107.1 ± 8.1 |
| 106.8 ± 6.2 | 112.9 ± 2.1 |
| 102.7 ± 1.1 | 91.7 ± 9.5* |

Conclusion

Sequential combination surprisingly showed antagonistic effects in W138 and in high concentrations of Cetuximab in HT29 and DLD1.

Example 4

Cetuximab and the Proliferation Activities of the cell line C205

Cetuximab and CHP Direct Combination

Cetuximab was diluted in twofold steps from 40 µg/ml to 1.25 µg/ml and CHP was used in direct combination with the monoclonal antibody at a concentration of 400 µg/ml (C205 comb). (*=significantly different)

| C205con | C205comb | CETUXIMAB |
|---|---|---|
| 100.1 ± 4.6 | 101.5 ± 4.6 | 40 |
| 103.1 ± 3.0 | 106.7 ± 5.3 | 20 |
| 99.1 ± 3.2 | 100.8 ± 5.8 | 10 |
| 100.7 ± 7.9 | 108.6 ± 0.7* | 5 |
| 101.7 ± 4.3 | 113.9 ± 11.3* | 2.5 |
| 101.6 ± 7.1 | 101.2 ± 2.8 | 1.25 |
| 98.0 ± 3.5 | 101.6 ± 4.2 | 0.6 |
| 104.2 ± 6.8 | 110.0 ± 4.7 | 0.3 |
| 94.8 ± 5.9 | 97.6 ± 6.5 | 0.15 |

Figure 5:
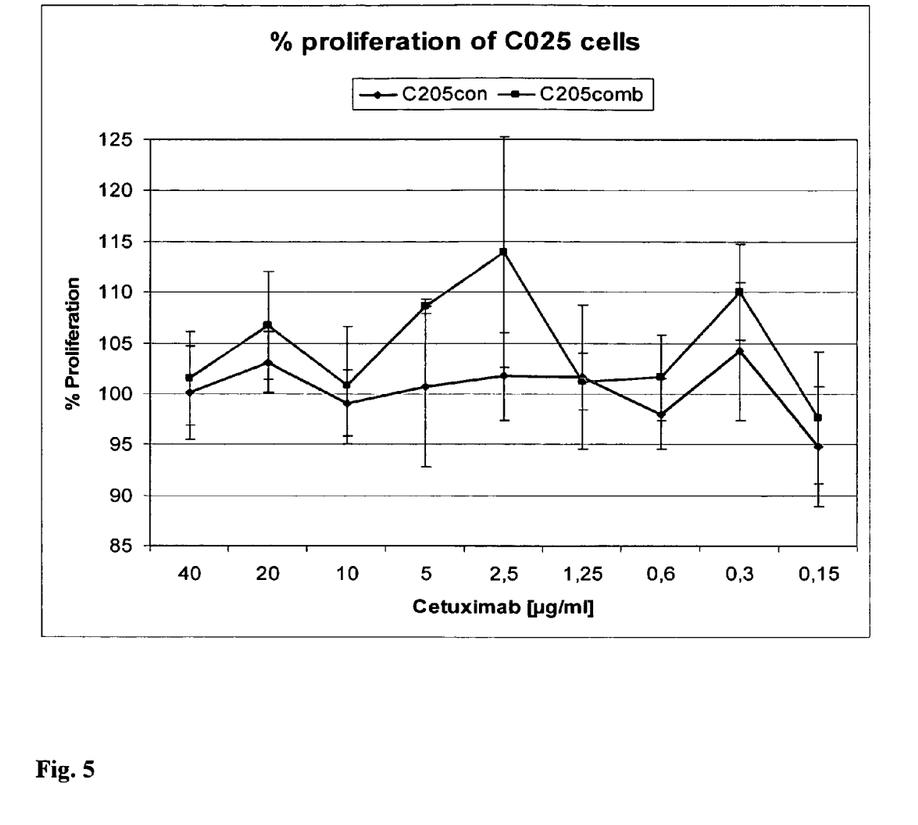
FIG. 5 shows the proliferation activities of C205 cells (in %) treated with a direct combination of Cetuximab and CHP (the concentration of Cetuximab was varied) in comparison to untreated control(s).

The results are depicted in FIG. 5.

Conclusion

In direct combination with Cetuximab, CHP is surprisingly antagonistic at low concentrations of CHP (5 and 2.5 µg/ml), whereas in other concentrations there was no significant interaction.

Example 5

Cetuximab and the Proliferation Activities of the Cell Lines BxPC3 and MIAPaCa2

Pre-Incubation with CHP 200 µg/ml

Experiments using pre-incubation with CHP were performed using more cell lines, namely BxPC3 and MIAPaCa2 pancreatic cancer cell lines. Cells were pre-treated using 200 µg/ml CHP for 5 days and the tested with Cetuximab (40-1.3 µg/ml). (*=significantly different)

| BxPC3con | BxPC3chp2 | MIAcon | MIAchp2 |
|---|---|---|---|
| 99.1 ± 5.9 | 100.2 ± 2.0 | 104 ± 6.8 | 106.2 ± 18.2 |
| 102.0 ± 7.1 | 97.1 ± 6.3 | 95.8 ± 10.5 | 103.8 ± 24.4 |
| 107.4 ± 14.6 | 92.3 ± 4.7* | 93.7 ± 3.3 | 120.2 ± 17.9* |
| 108.3 ± 13.3 | 96.6 ± 13.6 | 89.6 ± 11 | 101.5 ± 1.6* |
| 101.9 ± 9.3 | 98.0 ± 9.0 | 86.1 ± 2.9 | 105.0 ± 13.6* |
| 91.6 ± 0.5 | 85.1 ± 3.9 | 70.4 ± 3.8 | 80 ± 17.2 |

Conclusion

Surprisingly antagonistic interaction of CHP-Cetuximab in MIAPaCa2 has been observed.

Example 6

Cetuximab and the Proliferation Activities of the Cell Line C205 Following Pre-Incubation with CHP Derivatives The sensitivity of Colo 205 cells to Cetuximab was tested following pre-incubation of the cells with the respective derivative (A1.21, A1.23 and A2.23) for 5 days in tissue culture (50 µg/ml).

(*=significantly different)

| C205con | A1.21 | A1.23 | A2.23 |
|---|---|---|---|
| 97.9 ± 11 | 101.4 ± 2.1 | 107.1 ± 2.2 | 101.6 ± 5.9 |
| 95.9 ± 6.3 | 99.4 ± 2.1 | 107.05 ± 2.5* | 107.6 ± 5.5* |
| 96.5 ± 9.9 | 100.9 ± 1.9 | 99.0 ± 6.5 | 106.0 ± 9.1 |
| 94.9 ± 4.6 | 99.4 ± 3.0 | 99.9 ± 8.0 | 108.3 ± 10.3* |
| 95.4 ± 8.2 | 94.5 ± 1.7 | 104.8 ± 11.8 | 106.8 ± 12.9 |
| 93.1 ± 2.5 | 92.7 ± 2.5 | 93.9 ± 2.9 | 113.2 ± 13.9* |

A1.21 = 4-hydroxy-1-methyl-proline ethyl ester
A1.23 = 1-methyl-4-phenylamino-carbonyloxy-proline ethyl ester
A2.23 = 1-methyl-4-phenylamino-carbonyloxy-proline-isobutyl ester Conclusion Pre-treatment of Colo205 cells with each of the three derivatives tested here surprisingly did either not change the sensitivity of the cells to Cetuximab or was slightly antagonistic.

Example 7

Rituximab and the Proliferation Activities of the Cell Lines C205, CR02B and MIAPaCa-2 Following Pre-Treatment with CHP A panel of cell lines, namely CR02B carcinoid cells, MIAPaCa-2 pancreatic cancer and Colo205 colon cancer cells, were pre-treated with 400 µg/ml CHP (chp4) for 5 days in tissue culture and exposed to Rituximab (160-5 µg/ml). (*=significantly different)

| CRO2Bcon | CRO2Bchp4 | MIAcon | MIAchp4 |
|---|---|---|---|
| 105.3 ± 14.6 | 97.1 ± 1.7 | 97.1 ± 1.2 | 93.5 ± 1.8* |
| 97.1 ± 2.9 | 93.5 ± 2.2 | 95.8 ± 0.5 | 90.8 ± 0.1* |
| 95.5 ± 3.5 | 93.1 ± 1.2 | 95.5 ± 2.4 | 91.1 ± 0.6* |
| 92.8 ± 2.7 | 94.1 ± 3.1 | 96.0 ± 0.7 | 91.9 ± 2.0* |
| 94.3 ± 4.2 | 90.6 ± 1.1 | 93.7 ± 0.8 | 90.3 ± 2.0* |
| 100.2 ± 5.8 | 96.9 ± 1.4 | 97.3 ± 2.0 | 89.2 ± 4.9* |

| C205con | C205chp4 |
|---|---|
| 96.1 ± 1.6 | 85.0 ± 18.7 |
| 95.3 ± 1.1 | 85.0 ± 20.1 |
| 97.5 ± 1.1 | 83.9 ± 17.0 |
| 92.2 ± 7.4 | 81.7 ± 19.0 |
| 91.7 ± 10.3 | 78.5 ± 18.9 |
| 90.1 ± 6.5 | 74.8 ± 13.2 |

Conclusion

Cells are expected to be CD20-negative. Surprisingly showed synergy with CHP for MIAPaCa2.

Example 8

Avastatin and the Proliferation Activities of the Cell Lines C205, CR02B and MIAPaCa-2 Following Pre-Treatment with CHP The same cell lines as above (Rituximab) were pre-treated with CHP (chp4) and tested with Avastatin (200-6.3 µg/ml). (*=significantly different)

| CRO2Bcon | CRO2Bchp4 | MIAcon | MIAchp4 |
|---|---|---|---|
| 98.1 ± 0.6 | 94.9 ± 1.8* | 92.9 ± 1.0 | 92.6 ± 0.1 |
| 92.5 ± 0.6 | 92.1 ± 1.6 | 93.0 ± 1.5 | 88.6 ± 0.2* |
| 94.3 ± 2.0 | 92.9 ± 0.7 | 92.6 ± 0.5 | 89.4 ± 0.2* |
| 94.1 ± 4.3 | 91.9 ± 1.0 | 94.7 ± 1.5 | 85.7 ± 0.1* |
| 98.0 ± 1.1 | 93.8 ± 1.0* | 92.7 ± 0.5 | 93.8 ± 6.0 |
| 103.4 ± 1.4 | 101.2 ± 2.0 | 100.7 ± 2.0 | 94.3 ± 0.0* |

| C205con | C205chp4 |
|---|---|
| 96.8 ± .01 | 91.3 ± 4.2* |
| 92.0 ± 0.1 | 87.8 ± 1.8* |
| 94.7 ± 1.5 | 91.8 ± 3.3* |
| 97.1 ± 2.6 | 9.6 ± 5.1* |
| 98.1 ± 0.9 | 94.7 ± 4.2 |
| 100.2 ± 1.4 | 91.5 ± 13.0 |

Conclusion

Slightly synergistic effects of Avastatin-CHP pre-incubation in MIAPaCa2 and Colo205 at high concentrations of Avastatin.

Example 9

Experiments with analytical EGFR-Antibody in combination with CHP have been performed against colo250 colon cancer cell lines. The highest concentration of the antibody was 0.25 µg/ml.

| CHP and/or combination | Inhibition of the control in % |
|---|---|
| CHP (concentration 200 µg/ml) | 7.3 ± 8.1 |
| Combination of CHP (concentration 200 µg/ml) + 0.25 µg/ml of EGFR-antibody | 34.6 ± 11.0 |
| CHP (concentration 100 µg/ml) | 2.9 ± 10.1 |
| Combination of CHP (concentration 100 µg/ml) + 0.25 µg/ml of EGFR-antibody | 7.6 ± 11.6 |

Conclusion

Surprisingly the concentration of CHP at a concentration of 200; g/ml and EGFR-antibody at a concentration of 0.25 µg/ml have shown a high proliferation effect of 34.6±11%

The invention claimed is:

1. A composition comprising of cis-4-hydroxy-L-proline (CHP) together with bevacizumab and, optionally, a pharmaceutically acceptable carrier, excipient or diluent.

2. A kit comprising cis-4-hydroxy-L-proline (CHP) and bevacizumab, wherein the cis-4-hydroxy-L-proline (CHP) is kept in a separate container to bevacizumab, and information about using parts of the kit.

3. A pharmaceutical composition comprising
   (i) cis-4-hydroxy-L-proline (CHP); and
   (ii) bevacizumab.

* * * * *